(12) United States Patent
Martin et al.

(10) Patent No.: US 9,201,034 B2
(45) Date of Patent: Dec. 1, 2015

(54) METHODS AND DEVICES FOR DETERMINING SENSING DEVICE USABILITY

(75) Inventors: Glenn Martin, Ottawa (CA); Yi Wang, San Ramon, CA (US); Simon Tonks, Abingdon (GB); Benjamin J. Feldman, Oakland, CA (US)

(73) Assignee: Abbott Point of Care Inc., Princeton, NJ (US)

( * ) Notice: Subject to any disclaimer, the term of this patent is extended or adjusted under 35 U.S.C. 154(b) by 259 days.

(21) Appl. No.: 13/537,983

(22) Filed: Jun. 29, 2012

(65) Prior Publication Data

US 2013/0002278 A1   Jan. 3, 2013

Related U.S. Application Data

(60) Provisional application No. 61/579,247, filed on Dec. 22, 2011, provisional application No. 61/503,234, filed on Jun. 30, 2011.

(51) Int. Cl.
| | |
|---|---|
| *G01R 31/3187* | (2006.01) |
| *G01N 27/00* | (2006.01) |
| *G01N 27/04* | (2006.01) |

(52) U.S. Cl.
CPC .................................. *G01N 27/048* (2013.01)

(58) Field of Classification Search
CPC .... A61B 2562/029–2562/0295; A61B 5/1411; A61B 5/15142–5/15146; G01N 27/121; G01N 2201/1214; G01N 27/048
See application file for complete search history.

(56) References Cited

U.S. PATENT DOCUMENTS

| | | | |
|---|---|---|---|
| 3,922,431 A | 11/1975 | Radmacher et al. | |
| 3,942,467 A | 3/1976 | Witonsky | |
| 3,983,527 A * | 9/1976 | Ohsato et al. | ................... 338/35 |
| 4,059,406 A | 11/1977 | Fleet | |
| 5,096,669 A | 3/1992 | Lauks et al. | |
| 5,209,931 A | 5/1993 | Levin | |

(Continued)

FOREIGN PATENT DOCUMENTS

| | | |
|---|---|---|
| CN | 1427770 A | 7/2003 |
| CN | 101815936 A | 8/2010 |

(Continued)

OTHER PUBLICATIONS

International Search Report and Written Opinion for PCT/US2012/044905 mailed Oct. 5, 2012.

(Continued)

*Primary Examiner* — Patrick Assouad
*Assistant Examiner* — Haidong Zhang

(57) ABSTRACT

Methods and devices for determining sensing device usability, e.g., for self-monitoring and point of care devices. In one embodiment, the invention is to a method of determining device usability, comprising the steps of providing a device comprising a first electrical pad; a second electrical pad; and a humidity-responsive polymer layer contacting at least a portion of the first and second electrical pads; applying a potential across the first and second electrical pads; measuring an electrical property associated with the humidity-responsive polymer layer; and determining whether the measured electrical property associated with the humidity-responsive polymer layer has exceeded a humidity threshold level associated with the device usability.

14 Claims, 4 Drawing Sheets

(56) References Cited

U.S. PATENT DOCUMENTS

| | | | |
|---|---|---|---|
| 5,273,640 | A | 12/1993 | Kusanagi et al. |
| 5,554,339 | A | 9/1996 | Cozzette et al. |
| 6,063,486 | A | 5/2000 | Kobayashi |
| 6,158,381 | A | 12/2000 | Bray |
| 6,544,925 | B1 | 4/2003 | Prusik et al. |
| 6,629,057 | B2 | 9/2003 | Zweig et al. |
| 7,418,285 | B2 | 8/2008 | Ghesquiere et al. |
| 7,612,325 | B1 | 11/2009 | Watkins, Jr. et al. |
| 7,723,099 | B2 | 5/2010 | Miller et al. |
| 8,835,180 | B2 | 9/2014 | Gryska et al. |
| 2003/0139903 | A1 | 7/2003 | Zweig et al. |
| 2003/0148530 | A1 | 8/2003 | Lauks |
| 2004/0256227 | A1 | 12/2004 | Shin et al. |
| 2006/0214312 | A1* | 9/2006 | Wu et al. .................. 257/787 |
| 2007/0132542 | A1* | 6/2007 | Beck et al. ................. 338/35 |
| 2007/0166831 | A1 | 7/2007 | Watkins et al. |
| 2008/0145277 | A1 | 6/2008 | Wohland |
| 2009/0022630 | A1 | 1/2009 | Hoenes et al. |
| 2009/0056644 | A1* | 3/2009 | Phillips et al. ............ 122/15.1 |
| 2009/0119047 | A1 | 5/2009 | Zelin et al. |
| 2009/0159442 | A1 | 6/2009 | Collier et al. |
| 2009/0182244 | A1 | 7/2009 | Hoenes |
| 2009/0184004 | A1* | 7/2009 | Chatelier et al. .......... 205/777.5 |
| 2010/0206749 | A1* | 8/2010 | Choi .......................... 205/777.5 |
| 2011/0105613 | A1* | 5/2011 | Reiner et al. ................ 514/567 |
| 2011/0155043 | A1 | 6/2011 | Haarer et al. |
| 2012/0108694 | A1 | 5/2012 | Malet et al. |
| 2013/0000378 | A1 | 1/2013 | Martin et al. |
| 2013/0002265 | A1 | 1/2013 | Martin et al. |
| 2013/0002279 | A1 | 1/2013 | Martin et al. |

FOREIGN PATENT DOCUMENTS

| | | |
|---|---|---|
| EP | 2098857 | 9/2009 |
| WO | WO 2009/036429 | 3/2009 |
| WO | 2009/156285 A1 | 12/2009 |
| WO | 2010/086574 A2 | 8/2010 |

OTHER PUBLICATIONS

International Search Report and Written Opinion for PCT/US2012/044919 mailed Oct. 5, 2012.
International Preliminary Report on Patentability for PCT/US2012/044898 mailed Jan. 16, 2014.
International Preliminary Report on Patentability for PCT/US2012/044905 mailed Jan. 16, 2014.
International Preliminary Report on Patentability for PCT/US2012/044909 mailed Jan. 16, 2014.
International Preliminary Report on Patentability for PCT/US2012/044919 mailed Jan. 16, 2014.
Heller, et al., "Electrochemical Glucose Sensors and Their Applications in Diabetes Management", Chemical Reviews, vol. 108, No. 7, Jul. 1, 2008, pp. 2482-2505.
I-STAT System Manuel (2004) Abbott Point of Care.
International Search Report and Written Opinion for PCT/US2012/044898 mailed Oct. 5, 2012.
International Search Report and Written Opinion for PCT/US2012/044909 mailed Oct. 5, 2012.
Office Action for U.S. Appl. No. 13/538,218 dated Oct. 2, 2014.
First Office Action mailed Sep. 22, 2014 in CN Patent Application No. 201280039929.4, 14 pages.
First Office Action mailed Oct. 13, 2014 in CN Patent Application No. 201280039926.0, 16 pages.
Non-Final Office Action mailed Mar. 20, 2015 in U.S. Appl. No. 13/538,148, 20 pages.
Final Office Action mailed Apr. 15, 2015 in U.S. Appl. No. 13/538,218, 14 pages.
Chinese Office Action mailed on Jun. 26, 2015 for CN Patent Application No. 201280039926.0, with English translation, 9 pages.
Notice of Allowance mailed on Aug. 24, 2015 for U.S. Appl. No. 13/538,148, 11 pages.

* cited by examiner

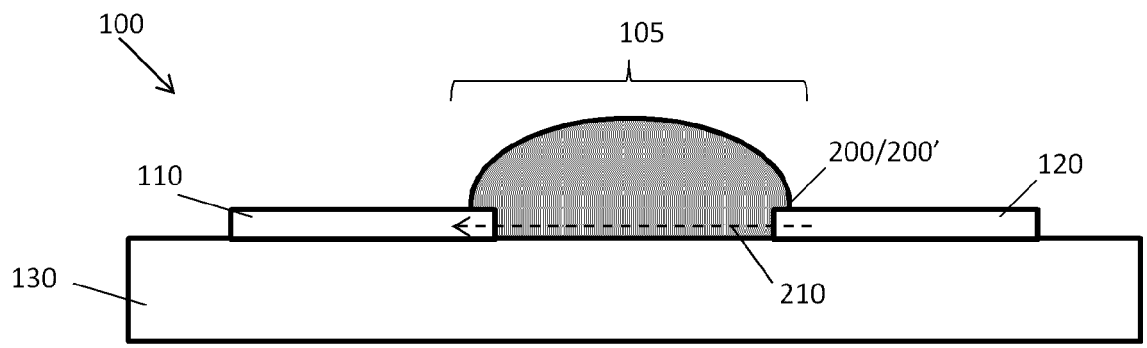
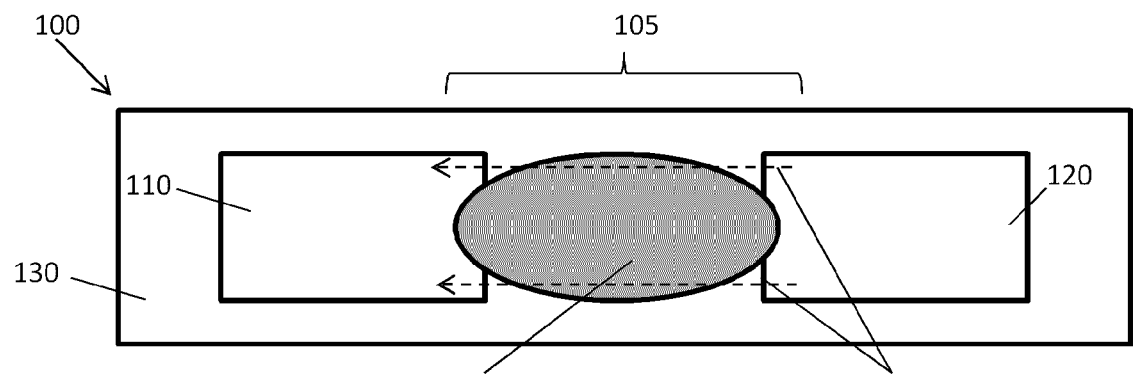
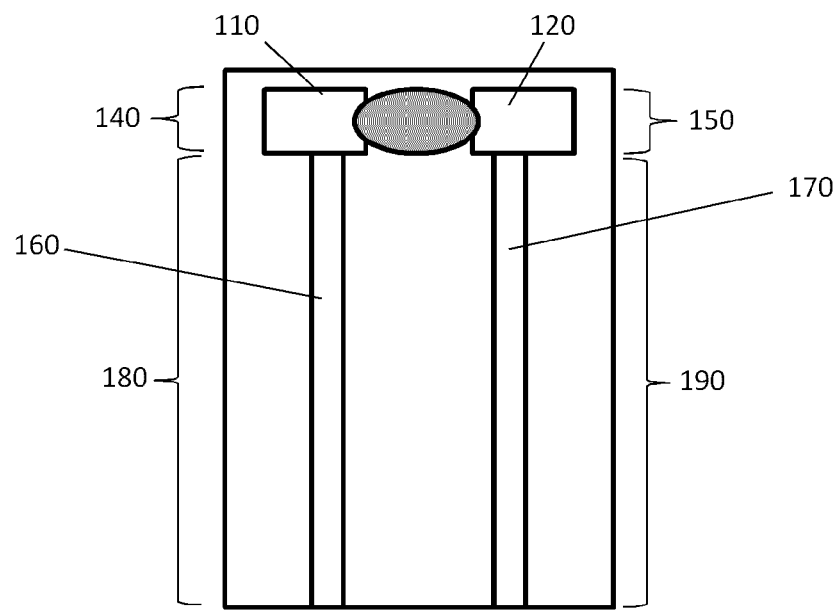
Fig. 3a
Fig. 3b
Fig. 3c

METHODS AND DEVICES FOR DETERMINING SENSING DEVICE USABILITY

CROSS REFERENCE TO RELATED APPLICATIONS

This application claims priority to U.S. Provisional Application No. 61/579,247, filed on Dec. 22, 2011, and to U.S. Provisional Application No. 61/503,234, filed on Jun. 30, 2011, the entireties of which are incorporated herein by reference.

FIELD OF THE INVENTION

The present invention relates to methods for determining device usability. In particular, the invention relates to such methods involving the application of a potential across a continuous polymer matrix and measuring an electrical property to determine whether the device has exceeded a threshold level associated with device usability.

BACKGROUND OF THE INVENTION

A multitude of self-monitoring and laboratory tests for analytes of interest are performed on biological samples for diagnosis, screening, disease staging, forensic analysis, pregnancy testing, and drug testing, among others. While a few qualitative tests, such as glucose, prothrombin and pregnancy tests, have been reduced to simple kits for a patient's home use, the majority of quantitative tests still require the expertise of trained technicians in a laboratory setting using sophisticated instruments. Laboratory testing increases the cost of analysis and delays the patient's or clinician's receipt of the results. In many circumstances, this delay can be detrimental to the patient's condition or prognosis, such as for example the analysis of markers indicating myocardial infarction and heart failure. In these and similar critical situations, it is advantageous to perform such analyses at the point-of-care, accurately, inexpensively and with minimal delay.

Self-monitoring tests are generally performed using in-home sample analysis systems, e.g., blood glucose monitoring devices. In-home analysis systems generally include a reusable reading apparatus that performs sample tests using a plurality of disposable devices (e.g., electrochemical test sensors or test strips) that can be loaded into the reading apparatus. An example of such a system is the PRECISION™ line of blood glucose and ketone body monitoring systems sold by Abbott Diabetes Care, Inc., Alameda, Calif., USA. Each individual electrochemical test sensor typically includes a substrate that is formed as a thin, rectangular strip of non-conductive material, and a plurality of carbon-layer electrodes deposited on the substrate with one electrode functioning as the reference electrode and one electrode functioning as the working electrode for the test sensor. In a reaction area of the substrate, an enzyme is deposited on the working electrode, and when the patient sample is exposed to the enzyme, the analyte, e.g., glucose, undergoes a chemical reaction, which produces a measurable electrical response.

Point-of-care sample analysis systems are generally based on a reusable reading apparatus that performs sample tests using a disposable device (e.g., a cartridge or strip) that contains analytical elements (e.g., electrodes or optics for sensing analytes such as, for example, pH, oxygen, glucose, or ketone body). The disposable device can optionally include fluidic elements (e.g., conduits for receiving and delivering the sample to the electrodes or optics), calibrant elements (e.g., fluids for standardizing the electrodes with a known concentration of the analyte), and dyes with known extinction coefficients for standardizing optics. In operation, the user may select a disposable device with the required panel of tests (e.g., electrolytes, metabolites, cardiac markers and the like), draw a sample, dispense it into the device, optionally seal the device, and insert the device into the reading apparatus to communicate the data to an LIS/HIS for analysis. An example of such a system is the i-STAT® system sold by Abbott Point-of-Care, Inc., Princeton, N.J., USA. The i-STAT® portable blood analysis system typically comprises Wi-Fi-enabled reader instruments that work in conjunction with single-use blood testing cartridges that contain sensors for various analytes. For further information on the i-STAT® portable blood analysis system, see http://www.abbottpointofcare.com/.

Self-monitoring and point-of-care sample testing systems eliminate the time-consuming need to send a sample to a central laboratory for testing. For instance, self-monitoring generally requires frequent measurements of a concentration of a particular analyte in a body fluid e.g., blood, of a patient, and the in-home analysis systems allow the patient to obtain a reliable qualitative results frequently throughout the day. Additionally, point-of-care sample testing systems allow a user e.g. a nurse and physician, at the bedside of a patient, to obtain reliable, quantitative, analytical results, comparable in quality to that which would be obtained in a laboratory.

Analyzers for self-monitoring and point-of-care testing, such as a self-contained disposable sensing device or cartridge and a reader or instrument, are further described in U.S. Pat. No. 7,418,285 to Ghesquiere et al. and U.S. Pat. No. 5,096,669 to Lauks, et al., the entireties of which are incorporated herein by reference. In general operation of the analyzers, a fluid sample to be measured is drawn into a device and the device is inserted into the reader through a slotted opening. Data generated from measurements performed by the reader may be output to a display and/or other output device, such as a printer, or, as described in greater detail below, via a wireless network connection. The disposable device may contain sensing arrays and several cavities and conduits that perform sample collection, provide reagents for use in measurement and sensor calibration, and transport fluids to and from the sensors. Optionally, reagents may be mixed into the sample for testing. Sensing arrays in the device measure the specific chemical species in the fluid sample being tested. The electrochemical sensors are exposed to and react with the fluid sample to be measured generating electrical currents and potentials indicative of the measurements being performed. The electrochemical sensors may be constructed dry and when the calibrant fluid flows over the electrochemical sensors, the sensors easily "wet up" and are operational and stable for calibration and composition measurements. These characteristics provide many packaging and storage advantages, including a long shelf life. Each of the sensing arrays may comprise an array of conventional electrical contacts, an array of electrochemical sensors, and circuitry for connecting individual sensors to individual contacts. The electrical signals are communicated to a reader enabled to perform calculations and to display data, such as the concentration of the results of the measurement.

Although the particular order in which the sampling and analytical steps occur may vary between different self-monitoring systems, point-of-care systems, and providers, the objective of providing rapid sample test results in close proximity to a patient remains. The reading apparatus (e.g., Precision Xtra® Blood Glucose Monitoring System, i-STAT® analyzer or other analyzer) may then perform a test cycle (i.e., all the other analytical steps required to perform the tests). Such simplicity gives the patient or physician quicker insight into the patient's physiological status and, by reducing the time for monitoring or diagnosis, enables a quicker decision by the patient or physician on disease management or appropriate treatment, thus enhancing the likelihood of a successful patient treatment.

In the emergency room and other acute-care locations within a hospital, the types of sample tests required for individual patients can vary widely. Thus, point-of-care systems generally offer a range of disposable devices configured to perform different sample tests, or combinations of such tests. For example, for blood analysis devices, in addition to traditional blood tests, including oxygen, carbon dioxide, pH, potassium, sodium, magnesium, calcium, chloride, phosphate, hematocrit, glucose, urea (e.g., BUN), creatinine and liver enzymes, other tests may include, for example, prothrombin time (PT), activated clotting time (ACT), activated partial thromboplastin time (APTT), troponin, creatine kinase MB (CKMB), and lactate. Although devices typically contain between one and ten tests, it will be appreciated by persons of ordinary skill in the art that any number of tests may be contained in a device.

A given hospital may use numerous different types of test devices and test instruments at multiple point-of-care testing locations within the hospital. These locations can include, for example, an emergency room (ER), a critical care unit (CCU), a pediatric intensive care unit (PICU), an intensive care unit (ICU), a renal dialysis unit (RDU), an operating room (OR), a cardiovascular operating room (CVOR), general wards (GW), and the like. Other non-hospital-based locations where medical care is delivered, include, for example, MASH units, nursing homes, and cruise, commercial, and military ships.

In some cases, test strips and cartridges have a shelf life, which may vary widely depending on the specific test strip or cartridge as well as upon storage conditions. For example, some cartridges may have a shelf life of about six to about nine months when refrigerated, but a much more limited shelf life, e.g., about two weeks at room temperature, or, more specifically, about ten weeks at up to about 30° C. As a result, hospitals typically store cartridges at a central refrigerated location, and deliver cartridges to specific locations as demand requires. These locations can include, for example, an emergency room (ER), critical care unit (CCU), pediatric intensive care unit (PICU), intensive care unit (ICU), renal dialysis unit (RDU), operating room (OR), cardiovascular operating room (CVOR) and general wards (GW). These locations may or may not have available refrigerated storage, and this will impact product lifetime and, as a result, the inventory they will hold. Further complicating device management is the fact that a given user, such as the patient, may store the test strips in an improper manner, e.g., at an unsuitable temperature or humidity, or a user, such as a hospital, may use multiple types of cartridges, each having a different shelf life. Alternatively, the user may be a physician's office laboratory or visiting nurse service. However, the need to ensure quality remains the same.

U.S. Patent Appl. No. US 2009/0119047 to Zelin et al., the entirety of which is incorporated herein by reference, discloses an improved quality assurance system and method for point-of-care testing. It provides quality assurance for laboratory quality tests performed by a blood analysis system at the point of patient care without the need for running liquid-based quality control materials on the analysis system. Quality assurance of a quantitative physiological sample test system is performed without using a quality control sample by monitoring the thermal and temporal stress of a component used with the test system. Alert information is generated that indicates that the component has failed quality assurance when the thermal and temporal stress exceeds a predetermined thermal-temporal stress threshold.

U.S. Pat. No. 7,612,325 to Watkins Jr., et al., the entirety of which is incorporated herein by reference, discloses electrical sensor for monitoring degradation of products from environmental stressors and describes an environmental degradation sensor for environmentally sensitive products such as food, pharmaceuticals or cosmetic products provides the degraded state and estimated remaining life of the product. The sensor is made of a polymeric matrix and conductive filler. A control agent, selected to adjust a reaction rate of the sensor to environmental conditions, allows correlation of an electrical property of the sensor to a degraded state of the product.

Application Note 2004-2, "A Comparison of Relative Humidity Sensing Technologies," Hygrometrix Inc., 2004, the entirety of which is incorporated herein by reference, discloses that the transduction of water vapor concentration into an electrical measurement by a sensing film comprises three processes: (i) physical and chemical interaction of water vapor molecules with the film surface; (ii) surface and bulk modifications of the film due to water vapor accumulation on and diffusion into the film; and (iii) electrical measurement of a key electrical or mechanical property of the film that changes due to its interaction with water vapor. The sensing films are typically made of polyelectrolyte, polymers, and porous ceramic.

In general, the principles of operation for existing types of time/temperature and time/humidity indicators can be categorized as physical, chemical and electrical. Examples of physical and chemical methods include color change of polymeric materials, chemical reactions of two elements, physical masking of a marker, melting of a temperature sensitive material and the like.

However, the use of many existing indicators adds significant cost and complexity to the devices they are intended to monitor. This is a particularly apparent issue for single-use blood testing cartridges and electrochemical strip devices, e.g., glucose blood testing strips used by diabetics. Consequently, the need remains for improved low cost time-temperature or time-humidity indicators that are amenable to direct integration into a device manufacturing work flow.

SUMMARY OF THE INVENTION

In one embodiment, the invention is to a method of determining device usability, comprising the steps of: providing a device comprising a first electrical pad; a second electrical pad; and a humidity-responsive polymer layer contacting at least a portion of the first and second electrical pads; applying a potential across the first and second electrical pads; measuring an electrical property, e.g., current, resistance, impedance, conductivity, or a combination thereof, associated with the humidity-responsive polymer layer; and determining whether the measured electrical property associated with the humidity-responsive polymer layer has exceeded a humidity threshold level associated with the device usability. Optionally, the method further comprises a step of measuring an initial current value associated with the humidity-responsive polymer layer when the device is manufactured and wherein the humidity threshold level is at least five times lower than the initial current value. As an alternative, the method may include a step of measuring an initial impedance value associated with the humidity-responsive polymer layer when the device is manufactured, wherein the humidity threshold level is at least five times greater than the initial impedance.

In one aspect, the potential comprises a sigmoidal potential cycle, a fixed applied potential, a sequence of fixed applied potential steps, or a combination thereof. The potential optionally comprises a potential cycle that is applied at a predetermined frequency in the range of about 1 Hz to about 100 Hz. The method optionally includes a step of inserting the device into an analyzer configured to determine whether the measured electrical property associated with the humidity-responsive polymer layer has exceeded the threshold level associated with the device usability.

In another embodiment, the invention is to a device having a usability threshold, comprising a first electrical pad, a second electrical pad, and a humidity-responsive polymer layer contacting at least a portion of the first and second electrical pads, wherein the humidity-responsive polymer layer has an electrical property associated with the device usability threshold.

In preferred embodiments, the polymer layer is selected from the group consisting of a crosslinked polyvinylpyrrolidone (PVP), a crosslinked polymer comprising nitrogen-containing heterocyclic groups described in, for example, U.S. Pat. No. 6,932,894, the disclosure of which is incorporated by reference in its entirety, as well as combinations thereof.

The configuration and shape of the polymer layer may vary widely, but in one embodiment, the continuous polymer layer is substantially circular, preferably domed, and has a diameter of from about 20 µm to about 5 mm. The device may further comprise a boundary structure for controlling the spreading of a dispensed polymer layer precursor to a predetermined region of the device, e.g., a ring intersecting said first and second contact pads. The first and second pads optionally are separated by a distance of from about 10 µm to about 4 mm.

The device may comprise a sensor selected from the group consisting of a pH sensor, oxygen sensor, carbon dioxide sensor, hematocrit sensor, glucose sensor, ketone body sensor, lactate sensor, creatinine sensor, sodium sensor, potassium sensor, magnesium sensor, calcium sensor, chloride sensor, phosphate sensor, liver enzyme sensor, BNP sensor, troponin sensor, BUN sensor, CKMB sensor, NGAL sensor, TSH sensor, D-dimer sensor, PSA sensor, PTH sensor, cholesterol sensor, ALT sensor, AST sensor, prothrombin sensor, APTT sensor, ACT sensor, galectin sensor, and combinations thereof.

In another embodiment, the invention is to a method of correcting a signal generated by an analyte sensor, comprising the steps of providing a device comprising a first electrical pad, a second electrical pad, and a humidity-responsive polymer layer contacting at least a portion of said first and said second electrical pads; applying a potential across said first and said second electrical pads; measuring an electrical property associated with said humidity-responsive polymer layer; determining a correction factor associated with said measured electrical property; and applying said correction factor to said signal generated by said analyte sensor to produce a corrected signal.

In another embodiment, the invention is to a glucose test strip comprising an integrated humidity detector, said glucose test strip including a glucose sensing electrode connected by a first conductive line to a first electrical contact pad; a reference electrode connected by a second conductive line to a second electrical contact pad; and a polymer layer that is responsive to humidity, which contacts at least a portion of said first and said second conductive lines.

In another embodiment, the invention is to a method of determining exposure of a glucose test strip to humidity, the method comprising inserting said glucose test strip into a glucose meter, said glucose test strip comprising a glucose sensing electrode connected by a first conductive line to a first electrical contact pad and a reference electrode connected by a second conductive line to a second electrical contact pad, wherein a polymer layer responsive to humidity positioned on said glucose test strip contacts at least a portion of said first and said second conductive lines; applying a potential across said polymer layer; measuring an electrical property associated with said polymer layer; and calculating a humidity exposure value from said electrical property.

In another embodiment, the invention is to a test strip comprising an integrated humidity detector for testing one or more analytes, said test strip including a strip with an analyte sensing electrode connected by a first conductive line to a first contact pad and a reference electrode connected by a second conductive line to a second contact pad; and a polymer layer responsive to humidity positioned on said test strip, which contacts at least a portion of said first and said second conductive lines, wherein said polymer layer has an electrical property associated with a usability threshold of said test strip.

In another embodiment, the invention is to a handheld electronic device comprising a strip port for receiving a test strip, wherein said test strip comprises a substantially planar strip including an analyte sensing electrode connected by a first conductive line to a first contact pad and a reference electrode connected by a second conductive line to a second contact pad; and a polymer layer responsive to humidity positioned on said test strip, which contacts at least a portion of said first and said second conductive lines, wherein said polymer layer has an electrical property associated with a usability threshold of said test strip; and a processor configured to determine whether said electrical property associated with said polymer layer has exceeded said usability threshold of said test strip.

In another embodiment, the invention is to an analyte testing system comprising a test strip comprising a substantially planar strip including an analyte sensing electrode connected by a first conductive line to a first contact pad and a reference electrode connected by a second conductive line to a second contact pad; and a polymer layer responsive to humidity positioned on said test strip, which contacts at least a portion of said first and said second conductive lines, wherein said polymer layer has an electrical property associated with a usability threshold of said test strip; and a handheld electronic device comprising a strip port for receiving said test strip, and a processor.

BRIEF DESCRIPTION OF THE DRAWINGS

The present invention will be better understood in view of the appended non-limiting figures, in which:

FIGS. 3a, 3b, and 3c show side and plane views of a time-humidity indicator (THI) device in accordance with one embodiment of the invention;

DETAILED DESCRIPTION OF THE INVENTION

Figure 1A:
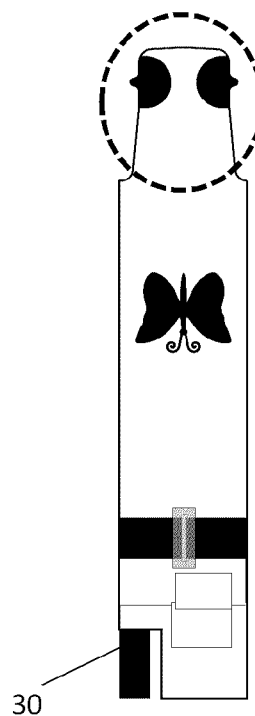
FIGS. 1a, 1b, and 1c present images showing test strips and parts thereof.

The present invention is best understood in the context of the current prior art on point-of-care blood analysis and self-monitoring systems. For example, the shelf life of an i-STAT® cartridge (see the i-STAT® system made by Abbott Point of Care, Princeton, N.J., USA) or a FreeStyle Lite® blood glucose test strips (see the FreeStyle Lite® system made by Abbott Diabetes Care Inc., Alameda, Calif., USA) is typically indicated by an expiration date on the product packaging. Specifically, with respect to the i-STAT® cartridge, a refrigeration expiration date and a room temperature shelf life are provided on the product packaging, e.g., on a fluid-containing pouch thereof. The refrigeration expiration date defines the length of time that the cartridge may be stored under refrigerated conditions after manufacture, e.g., at about 5° C. Depending on the specific device, the refrigeration expiration date may be about three months, about six months, about nine months or about one year after the date of manufacture. The room temperature shelf life defines the length of time that the cartridge may be stored under room temperature (ambient, e.g., 25° C.) conditions after a cartridge or a box of cartridges is removed from refrigeration conditions, i.e., removed from a refrigerator. The room temperature shelf life should not be allowed to exceed the refrigeration expiration date. The room temperature shelf life is typically on the order of from two to nine weeks, depending on cartridge type. In practice, the room temperature expiration date is calculated from the room temperature shelf life and is written on the box by the user at the time of removal from the fridge. Thus, when a box of cartridges is taken out of the refrigerator, the user typically counts the number of days or months to determine the room temperature expiration date, verifies that the room temperature expiration date does not exceed the refrigeration expiration date printed on the box or cartridge, and writes the room temperature expiration date down on the box. Furthermore, when a cartridge is to be used, the end user again checks the expiry dates. This process lends itself to potential user error in either or both calculating the refrigeration expiration date and/or verifying that the refrigeration expiration date has not been passed. The present invention is intended to determine the suitability of the cartridge or test strip for use, i.e., the non-expiration of the shelf life, automatically taking into consideration the age of the device as well as the environment, e.g., temperature and/or humidity, under which the device has been stored. Thus, the user is relieved of this task and the opportunity for a user-induced error is diminished.

While there are several time-temperature, time-humidity, or shelf life indicators that are known in the art, it is highly desirable to keep the cost and complexity of the device to a minimum. In the present invention this is achieved by providing (or modifying) a pair of electrical contact pads. Many analytical systems employ electrical or electrochemical principles and will already have such electrical contact pads as part of the device. Consequently, their use adds no cost as they are present and necessary for other functions, e.g., are used in analyte detection or in device calibration. The electrical contact pads are desirably modified so that they can act as shelf life indicators while still fulfilling their intended purpose, typically analyte detection or device calibration. Thus, the function of the shelf life indicator of the invention should also be conducted without diminishing the ability or performance of the contact pads for their primary purpose, e.g., signal transmission in analyte sensing or device calibration. It is also contemplated, however, that the electrical contact pads that are used for time/temperature or time/humidity indication according to some embodiments may be separately provided specifically for performing the role of a shelf life indicator, and do not provide any other role, e.g., in analyte sensing or device calibration. In this latter aspect, separate contact pads optionally may be provided for analyte detection and/or device calibration.

The present invention was in part stimulated by the observation that the electrical resistance of some prototype ion sensor membranes was found to change after being subjected to elevated humidity conditions for certain periods of time. The present invention is thus based on the changing electrical properties, e.g., current flow, resistance and the like, of a polymer layer or the like that is positioned between and preferably contacts two adjacent contact pads.

In the present specification, the material that is positioned between the two adjacent contact pads is referred to as a "THI material." The THI material is preferably responsive to the integral of varying humidity exposure, and optionally temperature exposure, over time such that this gives rise to a predictable change in an electrical property of the THI material. For example, in accordance with some aspects of the invention, a THI relationship between humidity exposure and change in electrical property may be established such that the electrical property e.g., conductivity or resistance, of the THI material depends upon an amount of water vapor accumulation on and diffusion into the THI material, e.g., the electrical property of the THI material changes due to its interaction with water vapor.

Devices suitable for use in the present invention include, but are not limited to, point-of-care and self-monitoring devices such as those disclosed in U.S. Pat. Nos. 7,723,099 and 7,802,467, the entireties of which are incorporated herein by reference. In one embodiment, the device comprises a first electrical pad and a second electrical pad in contact with a sensor. As used herein, the term "electrical pad" refers to a location wherein electricity may be applied to the device. The electrical pads of the present invention may, for example, comprise a metal contact comprising gold, silver, a combination thereof or another metal. Suitable sensors for use with the present invention include, but are not limited to, electrochemical sensors, amperometric sensors, potentiometric sensors and conductimetric sensors. Alternatively, neither of the electrical pads are associated with a sensor. For example, the device may have a sensor that is independent of the electrical pads.

Figure 1B:
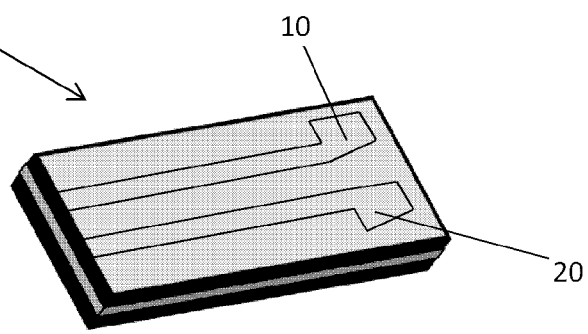
Figure 2:
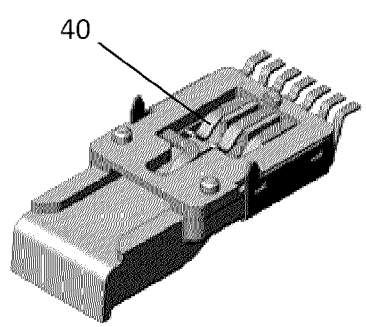
FIG. 2 presents an image showing a connector for a test strip and parts thereof.
Figure 1C:
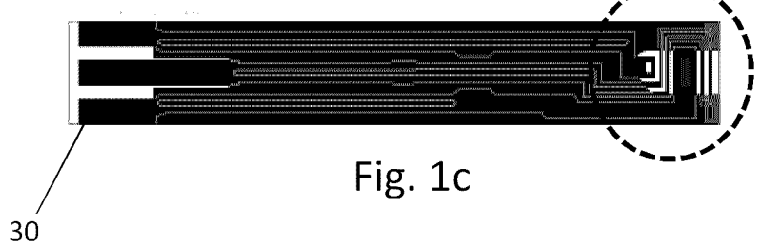

The present invention will be specifically described in the context of a glucose test strip, e.g., a FreeStyle Lite® blood glucose test strip, that employs at least two adjacent electrode pads 10 and 20 (e.g., a sensing electrode, a reference electrode, a working electrode, and/or a counter electrode), as shown in FIGS. 1a, 1b, and 1c. However, the invention is not limited to use with blood glucose strips and one of ordinary skill in the art would understand that the present invention could be used with many other devices, e.g., an i-STAT cartridge that employs at least two adjacent electrode pads, e.g., hematocrit (Hct) electrode pads, or a Hct pad adjacent to an amperometric sensor pad.

In accordance with some aspects of the invention, each electrode pad (or bar) terminates in an electrical contact 30, which is used to make contact with the connector 40 in a FreeStyle Lite® blood glucose reader, as shown in FIGS. 1a, 1c, and 1d. Features of the connectors are described in US Pat. Pub. No. 2011/0184264, the entirety of which is incorporated herein by reference. As indicated above, the primary functions of integrity checking and blood glucose measurement should not be affected by the additional use of the electrode pads as part of a shelf life indicator.

In a first embodiment, the present invention relates to a method for determining device usability with a time/humidity indicator (THI). In one embodiment, the method comprises the steps of providing a device comprising a first electrical pad, a second electrical pad, and a THI material (preferably a continuous humidity-responsive polymer layer) contacting at least a portion of the first and second electrical pads; applying a potential across the first and second electrical pads; measuring an electrical property associated with the THI material; and determining whether the measured electrical property associated with the THI material has exceeded a threshold level associated with the device usability.

In one aspect, as shown in FIGS. 3a and 3b, a THI device 100 for determining device usability comprises a polymer layer 105 formed in electrical contact with contact pads 110 and 120. The contact pads 110 and 120 may further be in contact with a substrate or base 130 (optionally a sensor). As shown, the contact pads 110 and 120 may comprise terminal portions 140 and 150 of contact lines 160 and 170. In another embodiment, not shown, the polymer layer is in electrical contact with non-terminal portions 180 and 190 of contact lines 160 and 170. Thus, the polymer layer (THI material) may be disposed between and in electrical contact with two electrical pads, which may comprise a pair of contact pads, a pair of non-terminal contact lines, or a combination thereof.

As shown in FIGS. 3a and 3b, the THI material 200 may be formed by depositing a THI material precursor 200' between the two contact pads 110 and 120. The THI material 200 may comprise a polymer layer, preferably a continuous polymer layer, and the THI material precursor 200' may comprise a polymer layer precursor. For example, the THI material 200 may be formed by depositing, e.g., printing, the THI material precursor 200', e.g., polymer layer precursor, between and preferably overlapping at least respective portions of the two contact pads 110 and 120, e.g., a working electrode and a counter electrode.

The THI material precursor 200' may then optionally be treated, e.g., with heat or other radiation, or dried to form the THI material 200, e.g., continuous polymer layer, in a region between the two contact pads 110 and 120, and preferably overlapping at least respective portions of the contact pads 110 and 120. This configuration enables the reader instrument to measure an electrical property of the THI material 200 before any sample or calibrant fluid contacts the contact pads 110 and 120, which are located in a fluid conduit within the test strip. See, for example, jointly owned U.S. Pat. Nos. 7,802,467 and 7,866,026, the entireties of which are incorporated herein by reference.

In some embodiments, the THI material 200 may comprise a continuous humidity-responsive polymer layer that includes a polymer matrix. In one embodiment, the polymer matrix is a crosslinked polymer comprising nitrogen-containing heterocyclic groups (such as those described in, for example, U.S. Pat. No. 6,932,894, incorporated herein by reference in its entirety). As an example, the polymer matrix may comprise a crosslinked polyvinylpyrrolidone (PVP), optionally of the type shown in Formula I, below, wherein m ranges from 1 to 4 mol % or is about 2.8 mol %, and n ranges from 96 to 99 mol % or is about 97.2 mol %.

Formula I

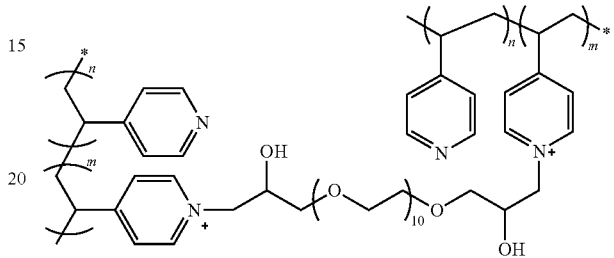

In another embodiment, the polymer matrix comprises a crosslinked polymer comprising nitrogen-containing heterocyclic groups of the type shown in Formula II below. In Formula (II), m optionally ranges from 10 to 30 mol % or about 20 mol %, n optionally ranges from 65 to 85 mol % or about 76 mol %, o optionally ranges from 0.5 to 3 mol % or about 1.2 mol %, and p optionally ranges from 1 to 5 mol % or about 2.5 mol %. Polymers crosslinked with poly(ethylene glycol) type crosslinkers are preferred, optionally poly(ethylene glycol)(400)diglycidyl ether (PEG400).

Formula II

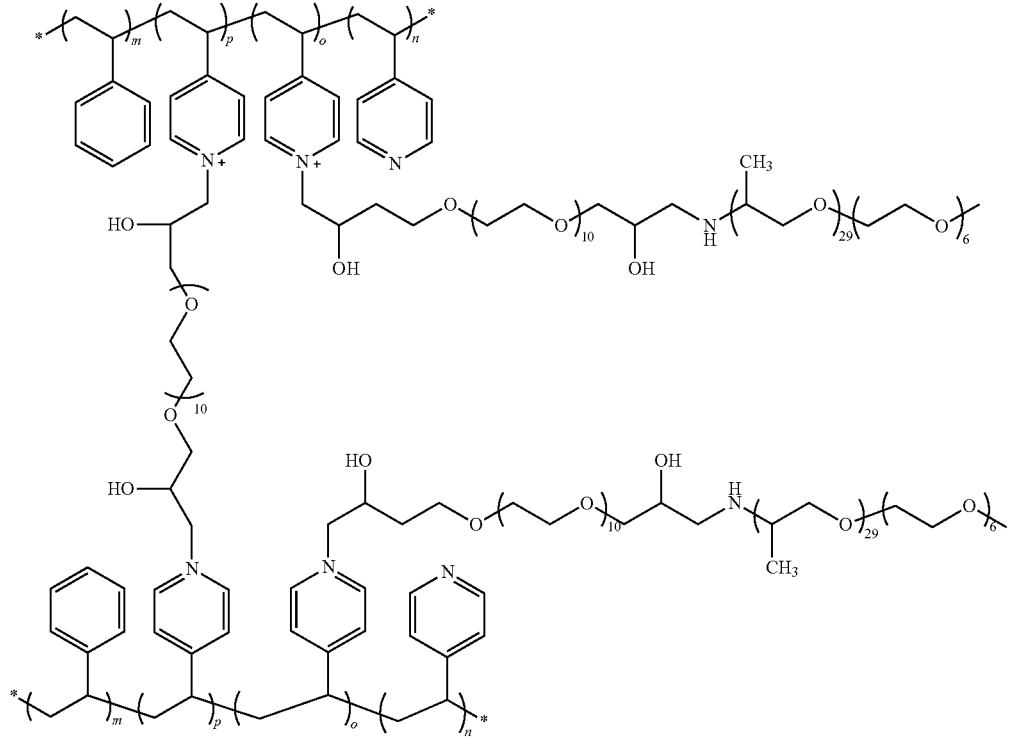

In another embodiment, the polymer matrix comprises a crosslinked polymer comprising nitrogen-containing heterocyclic groups, wherein the crosslinker comprises triglycidyl glycerol. An exemplary polymer of this type is shown in Formula III below, wherein o ranges from 5 to 15 mol % or is about 10 mol %, p ranges from 65 to 75 mol % or is about 69 mol %, y ranges from 5 to 15 mol % or is about 10 mol %, z ranges from 0.1 to 1 mol % or is about 0.6 mol %, and m ranges from 5 to 15 mol % or is about 10 mol %.

metallic oxide, semi-conductor particles, to adjust the initial resistivity to the desired level. By contrast, the present invention, in some aspects, relies on a THI material comprising a polymer, i.e., a non-conductive material, and hydronium and hydroxyl ions derived from atmospheric moisture (humidity). While hydronium and hydroxyl ions may be polar or ionic and thus affect the conductivity of the THI material, they are not particulate in nature. Nevertheless, in other aspects of the invention, such conductive particles may be included in the Formula III

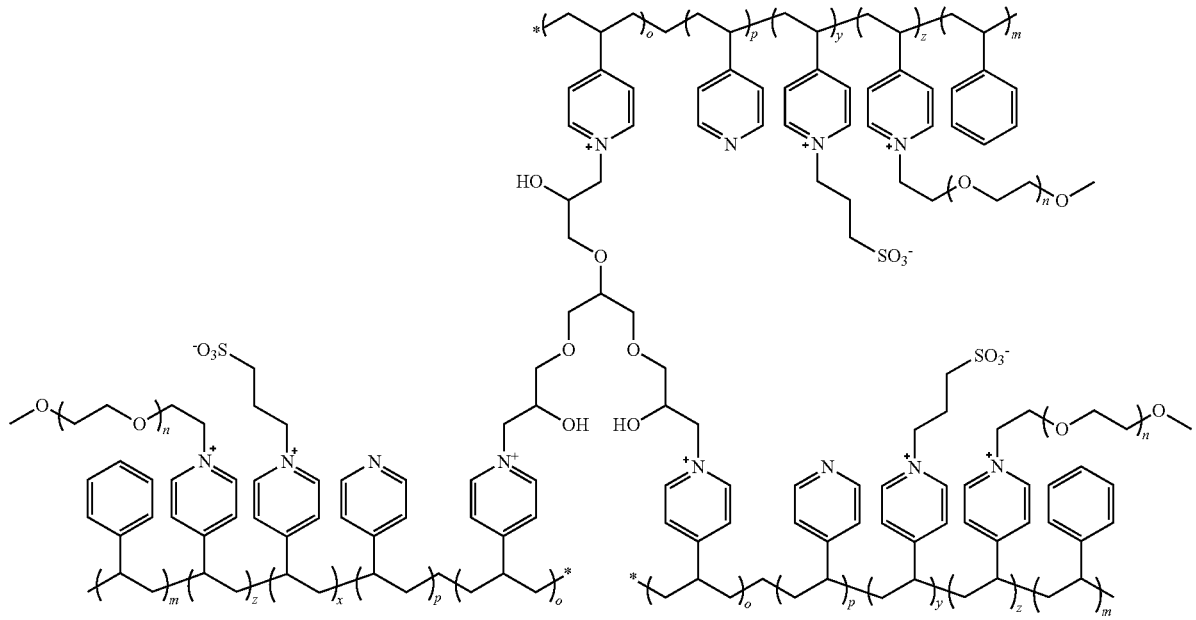

In another embodiment, the THI material comprises a polyurethane-acrylate based film, such as those described in Bosch et al., "Polyurethane-acrylate based films as humidity sensors," Polymer 46 at 12200-12209 (2005), incorporated herein by reference in its entirety.

The specific composition of the THI material precursor 200', e.g., polymer layer precursor, that is used to form the THI material, e.g., continuous humidity-responsive polymer layer, may vary widely. In an exemplary embodiment, the THI material precursor 200' may comprise the polymer matrix, as discussed above, but preferably further comprises a carrier medium (e.g., solvent) for imparting the desired physical properties for deposition thereof as well as solubilizing the polymer contained therein. In another embodiment, the precursor comprises a monomer and an initiator, and polymerization may occur after deposition of the THI material precursor 200' onto the surface, e.g., through free radical polymerization, optionally with application of UV radiation.

The carrier medium may comprise water or an organic solvent. As these materials are preferably microdispensed onto the contact pads using microdispensing methods and equipment as described in jointly owned U.S. Pat. No. 5,554,339 previously incorporated herein by reference, similar considerations as to ingredients, viscosity, surface preparation and pretreatment and the like also apply to the present invention.

The present invention advantageously avoids the need to add conductive particles to the THI material, e.g., carbon black, conductive carbon nanotubes, metallic particles, THI material precursor as well as the THI material used in the devices and methods of the invention.

As illustrated in FIGS. 3a and 3b, as time increases from the date of manufacture of the device 100 and/or as humidity increases, water vapor from the atmosphere may diffuse into the THI material 200 such that the conductivity of the THI material 200 increases over time and/or as humidity increases due to the dissociation of the water molecules into hydronium and hydroxyl ions within the THI material 200. In some embodiments, a potential or potential cycle 210 may be used to take an initial measurement at the date of manufacture, which may indicate a high initial impedance value that would decrease as water vapor diffuses into the THI material 200 resulting in an increase in conductivity of the THI material 200.

In a preferred embodiment, the step of depositing, e.g., printing, the THI material precursor between the two pads may be accomplished by using a microdispensing process such as the one described in jointly owned U.S. Pat. No. 5,554,339, the entirety of which is incorporated herein by reference. This process involves preparing a fluid composition suitable for forming the polymer layer and loading it into a microsyringe assembly. The microsyringe assembly may comprise, for example, a reservoir, a microsyringe needle, a pump for delivering the THI material precursor from the reservoir to the microsyringe needle, and a multidirectional controller so that droplets may be brought into contact with the area between the pads. Automatic alignment of the needle tip to the dispensing location may be achieved in manufacturing, for example, using an optical recognition system using one or more fiduciary marks.

In a preferred embodiment, particularly for low-cost compatible manufacturing methods, the process of depositing the THI material precursor may be substantially similar to the printing process that is employed for the manufacture of sensing membranes onto electrodes (see, e.g., U.S. Pat. No. 5,554,339) and the printing of reagents onto surfaces or conduit walls of cartridge components for subsequent dissolution into a blood sample.

As described herein, the continuous polymer layer is preferably formed by microdispensing one or more drops of the precursor onto the surface and removing the carrier medium, optionally with heat, and/or drying the precursor to form the THI material. In some embodiments, the deposited precursor forms a substantially circular shape having a diameter in the range of from about 20 µm to about 5 mm, preferably from 100 µm to about 500 µm, and is generally domed, covering the distance between the two pads, which preferably is in the range of from about 10 µm to about 4 mm, preferably from about 10 µm to about 200 µm. The average thickness of the layer is generally in the range of from about 1 µm to about 200 µm, preferably from about 20 µm to about 60 µm. One skilled in the art will appreciate that shapes and ranges outside of those provided above may be employed, for example, for larger sensor devices such as some home use glucose testing strips the precursor may be deposited to form a substantially rectangular shape that has sides of length from about 20 µm to about 5 mm.

Figure 4A:
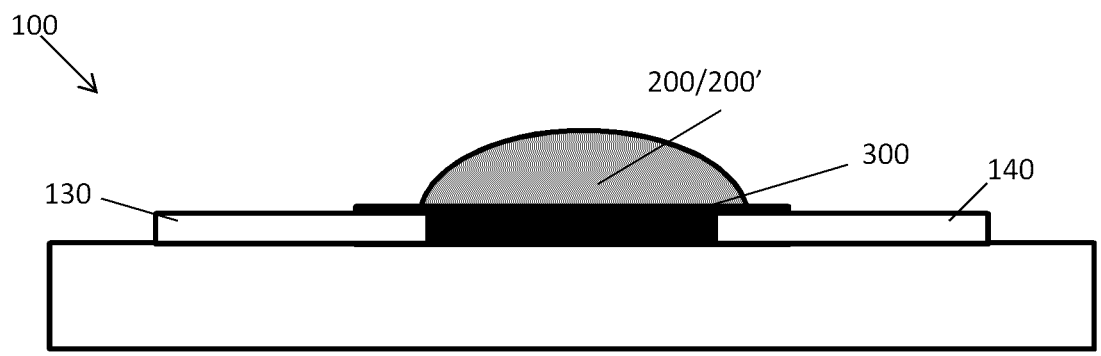
FIGS. 4a and 4b show side and plane views, respectively, of a THI device with a boundary structure in accordance with another embodiment of the invention.
Figure 4B:
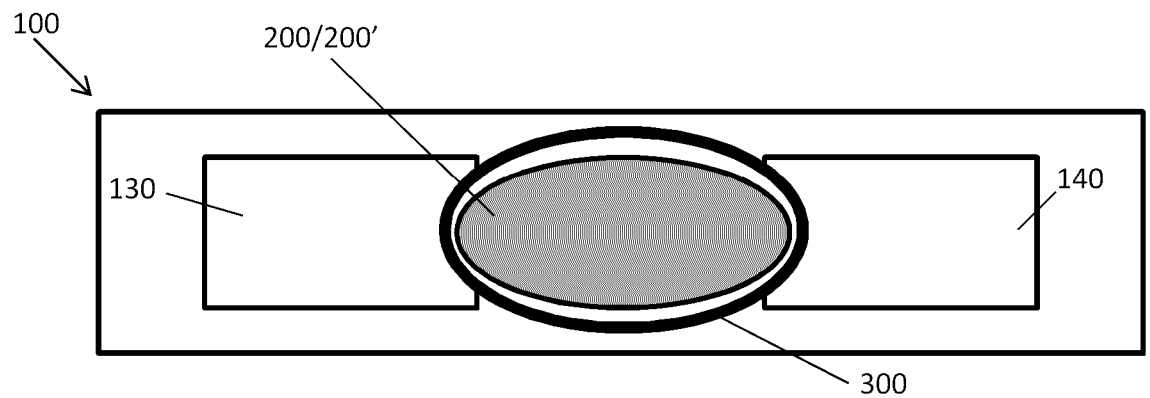

The THI material 200 preferably is accurately positioned in the device in order, for example, to avoid potential contamination of the connector, e.g., connector pins, in the instrument. Notably, the transfer of polymeric material from the THI material 200 to the connector pins should be minimized or avoided. Consequently, in some aspects, the present invention also relates to devices having a boundary structure 300, as shown in FIGS. 4a and 4b, that facilitates controlling the spreading of the dispensed precursor 200' that forms the THI material 200, e.g., continuous humidity-responsive polymer layer. The boundary structure 300 may, for example, be positioned at a predetermined region of the device 100, for example as a polygon, e.g., square, pentagon, hexagon, octagon, and the like, or as a cylindrical or ring shape. This boundary structure 300, if employed, preferably is positioned in a manner that intersects the two adjacent pads 130 and 140.

The boundary structure 300 may be formed, for example, by patterning a ridge of passivation material, e.g., a photoformable passivation material, such as a photoformable polyimide. The photoformable passivation material may be spin-coated and patterned to form an insulating layer over the contact lines on the chip. Thus, the mask for that process may also include the ring structures. Jointly owned U.S. Pat. No. 5,200,051, the entirety of which is incorporated by reference, discloses similar processes and photoformable materials. Other photoformable materials, e.g., those based on polyvinyl alcohol or dichromated gelatin, may also be used.

Figure 5:
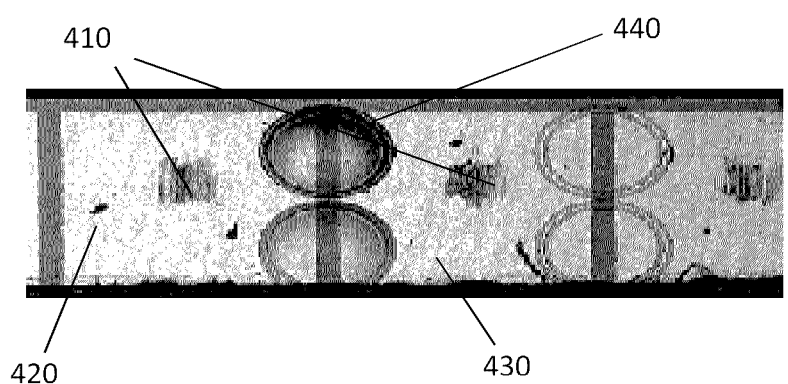
FIG. 5 presents an image showing a THI device deposited on first and second electrical pads in accordance with aspects of the invention.

In the above-described embodiments, connector pin tips may initially contact a top portion of the contact pads and move slightly towards the middle of the chip as the connector applies more force, it is preferred that the boundary structure 300, e.g., ring, be used for THI material 200 positions that are closer to the middle of the chip in order to properly locate the polymer layer. In this manner, the THI material preferably is positioned beyond the extent of travel of the pin tip, thus obviating the contamination issue. For example, the scratch marks 410 in the middle of the contact pads 420 and 430 in FIG. 5, show where the connector pins have hit the contact pads and moved during connector engagement in relationship to boundary structure 440.

In accordance with some aspects of the invention, the electrical property of the THI material that is measured may be the open circuit resistance ($R_{THI}$). If the electrical property, e.g., $R_{THI}$ measurement, does not exceed a predetermined threshold value or is within a certain range, the device, e.g., test strip, may be considered valid for use. For such test strips, depending on how an analyzer is programmed, the analyzer may indicate that the test strip has expired or otherwise reject the test strip and abort the test cycle, or engage in another remedial action, e.g., sensor output correction. Nevertheless, it should be understood, however, that such devices may still be suitable for use but may not have the desired degree of clinical precision.

While the present invention is conceived in the first embodiment as a process for determining device usability, in a second embodiment, the invention may be used for sensor correction. Thus, in the first embodiment, for example, the invention is to a device configured for determining device usability comprising a THI material, e.g., a continuous humidity-responsive polymer layer, formed on a substantially planar surface wherein the surface comprises two adjacent electrical contact pads. As indicated above, the THI material preferably covers at least a portion of the two electrical contact pads and a portion of the space on the surface between the contact pads. In a preferred embodiment, a preselected potential or potential cycle is applied to the pads and the impedance (Z) or current (I) associated with the THI material is measured, and the resulting measured value is compared with a predetermined threshold value to determine whether the device is usable.

In the second embodiment, the invention is to a device, a sensor, and a THI material, e.g., continuous humidity-responsive polymer layer, formed on a substantially planar surface wherein the surface comprises two adjacent electrical contact pads. The THI material covers at least a portion of the two electrical contact pads and a portion of the space on the surface between the contact pads. In operation, a preselected potential or potential cycle is applied to the contact pads and an electrical property, e.g., impedance or current, associated with the THI material is measured. The measured value is converted to a correction parameter that is applied to a signal from the output of the sensor to provide a corrected sensor signal.

In a related embodiment, the invention is to a method of correcting a signal in a sensing device, comprising the steps of: (a) providing a sensing device comprising a sensor, a first electrical pad, a second electrical pad, and a THI material, e.g., continuous humidity-responsive polymer layer, contacting at least a portion of the first and second electrical pads; (b) applying a potential across the first and second electrical pads; (c) measuring an electrical property associated with the THI material; (d) determining a correction factor associated with the measured electrical property, e.g., from a look up table or the like; and (e) applying the correction factor to a signal generated by the sensor to produce a corrected signal.

In order to determine the appropriate correction factor, e.g., from a look up table or correction algorithm, it is necessary to establish a relationship between the electrical property and the correction factors. Thus, in another embodiment, the invention is to a method of determining a correction factor comprising the steps of: (a) providing a plurality of devices, each of said devices comprising a sensor; a first electrical pad; a second electrical pad; and a continuous humidity-responsive polymer layer contacting at least a portion of the first and second electrical pads, wherein said devices have been exposed to different environmental conditions; (b) measuring an electrical property of the continuous polymer layer for each of the devices; (c) measuring a sensor signal for a control fluid for each of the devices; and (d) correlating the measured electrical properties with the measured sensor signals for the plurality of devices to determine the correction factor.

In a more generalized embodiment, the invention is to a device having a THI material, e.g., continuous humidity-responsive polymer layer, formed on a substantially planar surface, wherein the surface comprises two adjacent electrical contact pads. The THI material covers at least a portion of the two electrical contact pads and a portion of the space on said surface between said pads. When a preselected potential or potential cycle is applied to the contact pads and an electrical property, e.g., impedance or current, associated with the THI material is measured, the measured value determines whether the device is usable and, if the device is usable, whether it is necessary to correct the signal. If it is necessary to correct the signal, the device may determine the appropriate correction factor and modify a sensor signal from the device based on the correction factor to provide a corrected signal. For example a portion of a manufacturing lot of devices can be tested under different storage condition and tested with a standard liquid of known composition (control fluid). If the THI value and control fluid values are recorded, any variation between the expected and measured control fluid value can be correlated with the THI value and a correction algorithm created. This can then be implemented in the instrument when running real samples with that manufacturing lot of devices.

Various potential cycles may be used in measuring the electrical property associated with the THI material. In some exemplary embodiments, the potential cycle may be selected from a sigmoidal potential cycle, a fixed applied potential, and a potential that is a sequence of fixed applied potential steps. Measurements may be made, for example, with an impedance measuring circuit in an instrument, or a current measuring circuit in an instrument. In a preferred embodiment, an initial current value associated with the THI layer is measured when the device is manufactured and the threshold level is at least three times, preferably at least five times, lower than the initial current value. Conversely, in another aspect, an initial impedance value associated with the THI material is measured when the device is manufactured and the threshold level is at least three times greater, preferably at least five times greater, than the initial impedance. In some exemplary embodiments where current is measured, the current ranges from picoamps to milliamps, but more typically from nanoamps to microamps, e.g., from 0.1 to 100 nanoamps. Where impedance is measure, the typical impedance may range, for example, from below the megaohm range to above the gigaohm range, more typically in the tens of megaohms to low gigaohm range, optionally from 100 to 1500 megaohms at a frequency of from about 1 to about 10 Hz.

In embodiments where a sensor correction is made, the correction value may be selected from an amperometric correction value, a potentiometric correction value, a coulombic correction value and a conductivity correction value. These values are typically applied to a sensor selected from the group consisting of a pH sensor, oxygen sensor, carbon dioxide sensor, hematocrit sensor, glucose sensor, lactate sensor, creatinine sensor, sodium sensor, potassium sensor, magnesium sensor, calcium sensor, chloride sensor, phosphate sensor, liver enzyme sensor, BNP sensor, troponin sensor, BUN sensor, CKMB sensor, NGAL sensor, TSH sensor, D-dimer sensor, PSA sensor, PTH sensor, cholesterol sensor, ALT sensor, AST sensor, prothrombin sensor, APTT sensor, ACT sensor, galectin sensor, and combinations thereof.

The present invention may be easily adaptable to widely available commercial technologies and can be performed with existing electronics that require no hardware changes but only a software modification, which are generally simpler to implement than hardware modifications. For example, an i-STAT instrument may be able to measure conductivity at 10 kHz and 50 kHz, but may be conveniently expanded to a wider frequency range. In a preferred embodiment, this circuitry is programmed to measure the electrical resistance between adjacent contact pads at a frequency of 10 Hz. It has been found that low frequency impedance measurements in the range of from about 1 Hz to about 100000 Hz are most sensitive in detecting a change in the electrical property of the THI material.

Without being bound by theory, it is understood that changes in circuit impedance may be due to a change in the bulk membrane resistance, which is best observed when the ions in the membrane migrate some distance so they must be under a polarizing voltage for some time, which requires a low frequency. For example, water vapor may be adsorbed into the polymer layer and dissociated into hydronium and hydroxyl ions that decrease the bulk resistivity and accordingly increase conductivity of the polymer layer, which can be measured in terms of impedance or conductivity. One possible mechanism is that at higher frequencies, the voltage oscillates so quickly that the ions do not migrate appreciably. As a result, the resistance to their movement does not influence the impedance. Another possibility is that the impedance change over time that is observed in the present invention may be contributed in part by the electrode oxidation and its interface with the bulk polymer membrane. In general, electrode polarization impedance becomes more significant at lower frequencies than at higher frequencies. In any event, an important parameter to the present invention is an empirically observable and consistently predictable change in the electrical property.

To avoid compromising the use of the contact pads for their primary function, typically analyte sensing, where the electrical property that is measured is the open circuit resistance, the $R_{THI}$ preferably is much greater than, e.g., at least 1000 times greater than, the closed circuit resistance, i.e., the resistance measured between the electrodes attached to the contact pads with either sample or calibrant fluid covering the electrodes. However, the $R_{THI}$ preferably is much lower, e.g., at least 100 times lower, than the existing open circuit resistance, i.e., the resistance between the contact pins prior to contacting the pads. This goal may be accomplished through careful design of the geometry of the THI material and control of the THI composition. Thus, a reduced cross-sectional polymer layer area and an extended polymer pathlength between the pads will generally lead to an increased resistance for any given material composition, whereas increasing the ionic content and ion mobility of the polymer layer for a given geometry will generally lead to a decreased resistance. Note that the typical sample or calibrant fluid resistance is in the range of about ten to thousands of ohms, whereas the open circuit resistance is generally greater than several giga-ohms. Thus, the THI resistance is preferably in the mega-ohm to low giga-ohm range.

In one embodiment, a quantitative relationship between $R_{THI}$ and actual aging of a test strip may be established. As indicated herein, the objective is to prevent expired cartridges or test strips from being used and prevent usable cartridges or test strips from being discarded. Thus, in another embodiment, the invention is to a method of determining a threshold level associated with analytical device usability. The method comprises the steps of: (a) providing a plurality of devices, each of said devices comprising a sensor; a first electrical pad; a second electrical pad; and a continuous humidity-responsive polymer layer contacting at least a portion of the first and second electrical pads, wherein said devices have been exposed to different environmental conditions; (b) measuring an electrical property of the continuous polymer layer for each of the devices; (c) measuring a sensor signal for a control fluid for each of the devices; (d) identifying a subset of said plurality of devices that provide a signal having a predetermined acceptable precision level for said control fluid; and (e) determining the threshold level that corresponds to the electrical property of the continuous humidity-responsive polymer layer for the subset of said plurality of devices.

In accordance with some embodiments of the invention, the invention has the advantage that it enables a sensor that would otherwise have been considered to have exceeded its shelf life to still be used based on a time/temperature or time/humidity integrated correction factor. For example, once the THI relationship between water vapor (e.g., humidity) exposure and change in impedance has been established, a dynamic correction algorithm can be created and embedded into the instrument software.

An approach to correcting an assay result for aging may rely upon the following. The assay and THI need to predictably change when subjected to the same thermal or water vapor stress independent of the conditions to which it has been subjected. For example, an assay storage condition with highly fluctuating temperature or humidity (bounded by the allowable extremes) should produce nearly the same change as is observed when the assay is stored at a fixed temperature or humidity. If this condition is met, and if the time and mean kinetic temperature (MKT) or mean relative humidity (MRH), which is the equivalent fixed temperature or humidity at which an assay would need to be held to reach the same degree of aging, are known then the assay result can be corrected. If the duration of thermal or humidity stress is known (ideally the time since the date of manufacture), the THI can be used to calculate the MKT or MRH. Based upon the relationship established between the MKT or MRH and the change in the assay result, the expected change can be back calculated from the result. The correction algorithm may be derived using an Arrhenius model. For example, a correction factor for glucose may be determined by the following formula:

$$[Gluc] = b*response - c$$

wherein:
"response" is the slope of the sensor response (e.g., current) for the sample;
(b) is a calibration parameter for slope (b) of the sensor response;
(c) is a calibration parameter for intercept (c).

With aging, the response slope b is changing according to Arrhenius model and glucose concentration can be corrected as follows:

$$[Gluc] = \frac{b}{\theta_1 \cdot \exp\left(-\left(\theta_2 \cdot \exp\left(-\frac{Ea_{Gluc}}{R} \cdot \left(\frac{1}{MRH} - \frac{1}{H_{ref}}\right)\right)\right) \cdot time\right) + \theta_3} \times Response + c$$

wherein:
MRH is the mean relative humidity and can be estimated from the measured THI impedance $R_{THI}$;
$Ea_{Gluc}$ is apparent activation energy for change in glucose sensor response;
R is the universal gas constant;
$H_{ref}$ is the experimental reference humidity;
$\theta_1$ is a pre-exponential factor for time/humidity changes in b;
$\theta_2$ is the rate of change in b at $H_{ref}$; and
$\theta_3$ is non-humidity dependent offset=$1-\theta_1$.

Advantageously, by utilizing the present invention, it is possible to significantly further extend the time available for typical room storage of blood testing devices. In this context, the improvement can be at least about 50%. In addition, the invention may be applied to any electrochemical test device where the instrumentation enables current or impedance measurements, e.g., glucose meters used for diabetes monitoring with electrochemical sensor strips. The invention also simplifies the process of implementing point of care testing technology for the user, e.g., nurse, doctor or other healthcare professional. It also ensures that test devices, e.g., cartridges, strips and the like, have been stored properly prior to the use of each individual device. It can be used to compensate for device aging factors and improve the accuracy of results throughout the life of the device.

In another embodiment of the present invention, the measured value from the THI is used to calculate the remaining percentage of thermal or water vapor stress for the rest of a manufacturing lot of the same devices stored under the same conditions. This is essentially the length of time for room storage that remains for all of the other devices that were stored with the tested device but have yet to be used. As all of the devices in a given lot (e.g., a given FreeStyle Lite® blood glucose test strip manufacturing lot or a given i-STAT cartridge manufacturing lot) are manufactured in the same way and at the same time, the tested device gives a measured impedance or current value that not only is relevant to that particular device (as applied in other disclosed embodiments) but can also be used predictively with respect to other devices from the same manufactured lot that have been subjected to the same storage conditions as the tested device.

For example, assuming a water vapor stress budget of 100% at the time the lot of test strips are manufactured, at the time a particular test strip is tested, it is possible to calculate from the measured THI value that some fraction of the budget remains, i.e., a value from 100% to 0% (expiry). This is based on an embedded data curve reflecting this range that is part of the instrument software algorithm. The curve is derived from data, i.e., factory determined and uploaded to the instrument for predetermined lots.

Optionally, this information is displayed on the instrument and relayed to the hospital's point of care coordinator. This enables a new supply of devices, e.g., a new box of cartridges or test strips, to be ordered when expiry is imminent. It also enables the creation of a cartridge or test strip management report that allows the point of care coordinator to easily monitor and manage cartridges or test strips throughout a facility in a remote manner. Note that in practice, individual cartridges or test strips are generally traceable to a particular box and it is a reasonable assumption that cartridges or test strips are stored together in the box. Consequently, every time a cartridge or test strip is run from a particular box it provides useable information on the amount of room storage for the remaining cartridges or test strips in that box and all boxes stored similarly.

While the invention has been described in terms of various preferred embodiments, those skilled in the art will recognize that various modifications, substitutions, omissions and changes can be made without departing from the spirit of the present invention. Accordingly, it is intended that the scope of the present invention be limited solely by the scope of the following claims.

What is claimed is:

1. A method of determining device usability of an analyte sensing device, comprising the steps of:
    providing an analyte sensing device comprising a first electrical pad; a second electrical pad; and a humidity-responsive polymer layer contacting at least a portion of said first and said second electrical pads;
    applying a potential across said first and said second electrical pads, wherein the first electrical pad is connected to an analyte sensing electrode and the second electrical pad is connected to a reference electrode;
    measuring an electrical property associated with said humidity-responsive polymer layer; and
    determining whether said measured electrical property associated with said humidity-responsive polymer layer has exceeded a humidity threshold level associated with said analyte sensing device usability,
    wherein said humidity-responsive polymer layer is selected from the group consisting of a crosslinked polyvinylpyrrolidone (PVP), a crosslinked polymer containing nitrogen heterocyclic groups, and combinations thereof.

2. The method of claim 1, wherein said analyte sensing device is a glucose sensor or a ketone body sensor.

3. The method of claim 1, wherein said analyte sensing device is a sensor selected from the group consisting of a pH sensor, oxygen sensor, carbon dioxide sensor, hematocrit sensor, lactate sensor, creatinine sensor, sodium sensor, potassium sensor, chloride sensor, calcium sensor, BNP sensor, troponin sensor, CKMB sensor, NGAL sensor, TSH sensor, D-dimer sensor, PSA sensor, PTH sensor, cholesterol sensor, ALT sensor, AST sensor, prothrombin sensor, APTT sensor, ACT sensor, galectin sensor, and combinations thereof.

4. The method of claim 1, wherein said humidity-responsive polymer layer is substantially rectangular and has sides of length from about 20 µm to about 5 mm.

5. The method of claim 1, wherein said humidity-responsive polymer layer is applied to said device by a method selected from the group consisting of microdispensing, inkjet printing, and screen printing.

6. The method of claim 1, wherein said first electrical pad and said second electrical pad are separated by a distance of from about 10 µm to about 4 mm.

7. The method of claim 1, wherein said first electrical pad and said second electrical pad comprise terminal portions of contact lines.

8. The method of claim 1, wherein said first electrical pad and said second electrical pad comprise non-terminal portions of contact lines.

9. The method of claim 1, wherein said electrical property comprises current, resistance, impedance, conductivity, or combinations thereof.

10. The method of claim 1, wherein said potential comprises a sigmoidal potential cycle, a fixed applied potential, a sequence of fixed applied potential steps, or a combination thereof.

11. The method of claim 1, further comprising inserting said analyte sensing device into an analyzer configured to determine whether said measured electrical property associated with said humidity-responsive polymer layer has exceeded said humidity threshold level associated with said device usability.

12. A method of determining device usability of an analyte sensing device, comprising the steps of:
    providing an analyte sensing device comprising a first electrical pad; a second electrical pad; and a humidity-responsive polymer layer contacting at least a portion of said first and said second electrical pads;
    applying a potential across said first and said second electrical pads, wherein the first electrical pad is connected to an analyte sensing electrode and the second electrical pad is connected to a reference electrode;
    measuring an electrical property associated with said humidity-responsive polymer layer; and
    determining whether said measured electrical property associated with said humidity-responsive polymer layer has exceeded a humidity threshold level associated with said analyte sensing device usability,
    wherein said humidity-responsive polymer layer is substantially circular and has a diameter of from about 20 µm to about 5 mm.

13. A method of determining device usability of an analyte sensing device, comprising the steps of:
    providing an analyte sensing device comprising a first electrical pad; a second electrical pad; and a humidity-responsive polymer layer contacting at least a portion of said first and said second electrical pads;
    measuring an initial current value associated with said humidity-responsive polymer layer when said analyte sensing device is manufactured;
    applying a potential across said first and said second electrical pads, wherein the first electrical pad is connected to an analyte sensing electrode and the second electrical pad is connected to a reference electrode;
    measuring an electrical property associated with said humidity-responsive polymer layer; and
    determining whether said measured electrical property associated with said humidity-responsive polymer layer has exceeded a humidity threshold level associated with said analyte sensing device usability,
    wherein said humidity threshold level is at least five times higher than said initial current value.

14. A method of determining device usability of an analyte sensing device, comprising the steps of:
    providing an analyte sensing device comprising a first electrical pad; a second electrical pad; and a humidity-responsive polymer layer contacting at least a portion of said first and said second electrical pads;
    measuring an initial impedance value associated with said humidity-responsive polymer layer when said analyte sensing device is manufactured;
    applying a potential across said first and said second electrical pads, wherein the first electrical pad is connected to an analyte sensing electrode and the second electrical pad is connected to a reference electrode;
    measuring an electrical property associated with said humidity-responsive polymer layer; and
    determining whether said measured electrical property associated with said humidity-responsive polymer layer has exceeded a humidity threshold level associated with said analyte sensing device usability,
    wherein said humidity threshold level is at least five times lower than said initial impedance.

* * * * *